United States Patent
Dagger et al.

(10) Patent No.: US 10,117,782 B2
(45) Date of Patent: Nov. 6, 2018

(54) DEVICES AND METHODS FOR TREATING AND CLOSING WOUNDS WITH NEGATIVE PRESSURE

(71) Applicants: Smith & Nephew, Inc., Memphis, TN (US); University of Massachusetts, Boston, MA (US)

(72) Inventors: Anthony C. Dagger, York (GB); Nicholas Charlton Fry, Pocklington (GB); John Kenneth Hicks, Pocklington (GB); Elizabeth Mary Huddleston, Copmanthorpe (GB); Marcus Damian Phillips, Wakefield (GB); Carl Saxby, Brough (GB); Raymond M. Dunn, Shrewsbury, MA (US)

(73) Assignees: Smith & Nephew, Inc., Memphis, TN (US); University of Massachusetts, Boston, MA (US)

( * ) Notice: Subject to any disclaimer, the term of this patent is extended or adjusted under 35 U.S.C. 154(b) by 478 days.

(21) Appl. No.: 14/403,163

(22) PCT Filed: May 23, 2013

(86) PCT No.: PCT/IB2013/001555
§ 371 (c)(1),
(2) Date: Nov. 21, 2014

(87) PCT Pub. No.: WO2013/175309
PCT Pub. Date: Nov. 28, 2013

(65) Prior Publication Data
US 2015/0150729 A1 Jun. 4, 2015

Related U.S. Application Data

(60) Provisional application No. 61/782,270, filed on Mar. 14, 2013, provisional application No. 61/651,483, filed on May 24, 2012.

(51) Int. Cl.
*A61F 13/00* (2006.01)
*A61M 1/00* (2006.01)

(52) U.S. Cl.
CPC .. *A61F 13/00021* (2013.01); *A61F 13/00068* (2013.01); *A61M 1/0088* (2013.01)

(58) Field of Classification Search
CPC ........ A61F 13/00021; A61F 13/00068; A61M 1/0088
See application file for complete search history.

(56) References Cited

U.S. PATENT DOCUMENTS 3,194,239 A   7/1965   Sullivan
3,789,851 A   2/1974   LeVeen
(Continued)

FOREIGN PATENT DOCUMENTS

CN   101112326 A   1/2008
CN   101123930     2/2008
(Continued)

OTHER PUBLICATIONS

The Free Dictionary definition of "adhere," http://www.thefreedictionary.com/adhere.*
(Continued)

*Primary Examiner* — Adam Marcetich
*Assistant Examiner* — Jessica Arble
(74) *Attorney, Agent, or Firm* — Knobbe, Martens, Olson & Bear, LLP

(57) ABSTRACT

The present invention relates to a negative pressure wound closure system and methods for using such a system. Preferred embodiments of the invention facilitate closure of the wound by preferentially contracting to provide for movement of the tissue.

13 Claims, 21 Drawing Sheets

(56) References Cited

U.S. PATENT DOCUMENTS

| | | | |
|---|---|---|---|
| 4,467,805 | A | 8/1984 | Fukuda |
| 4,699,134 | A | 10/1987 | Samuelsen |
| 4,815,468 | A | 3/1989 | Annand |
| 5,176,663 | A * | 1/1993 | Svedman ............ A61F 13/0203 128/888 |
| 5,264,218 | A | 11/1993 | Rogozinski |
| 5,409,472 | A | 4/1995 | Rawlings et al. |
| 5,415,715 | A | 5/1995 | Delage et al. |
| 5,423,857 | A | 6/1995 | Rosenman et al. |
| 5,512,041 | A | 4/1996 | Bogart |
| 5,562,107 | A | 10/1996 | Lavendar et al. |
| 5,584,859 | A | 12/1996 | Brotz |
| 5,636,643 | A | 6/1997 | Argenta et al. |
| 5,695,777 | A | 12/1997 | Donovan et al. |
| 5,960,497 | A | 10/1999 | Castellino et al. |
| 6,080,168 | A | 6/2000 | Levin et al. |
| 6,086,591 | A | 7/2000 | Bojarski |
| 6,142,982 | A | 11/2000 | Hunt et al. |
| 6,176,868 | B1 | 1/2001 | Detour |
| 6,503,208 | B1 | 1/2003 | Skovlund |
| 6,548,727 | B1 | 4/2003 | Swenson |
| 6,553,998 | B2 | 4/2003 | Heaton et al. |
| 6,566,575 | B1 | 5/2003 | Stickels et al. |
| 6,685,681 | B2 | 2/2004 | Lockwood et al. |
| 6,695,823 | B1 | 2/2004 | Lina et al. |
| 6,712,830 | B2 | 3/2004 | Esplin |
| 6,767,334 | B1 | 7/2004 | Randolph |
| 6,770,794 | B2 | 8/2004 | Fleischmann |
| 6,776,769 | B2 | 8/2004 | Smith |
| 6,787,682 | B2 | 9/2004 | Gilman |
| 6,814,079 | B2 | 11/2004 | Heaton et al. |
| 6,893,452 | B2 | 5/2005 | Jacobs |
| 6,936,037 | B2 | 8/2005 | Bubb |
| 6,951,553 | B2 | 10/2005 | Bubb et al. |
| 6,977,323 | B1 | 12/2005 | Swenson |
| 6,994,702 | B1 | 2/2006 | Johnson |
| 7,004,915 | B2 | 2/2006 | Boynton et al. |
| 7,025,755 | B2 | 4/2006 | Epstein |
| 7,070,584 | B2 | 7/2006 | Johnson et al. |
| 7,117,869 | B2 | 10/2006 | Heaton et al. |
| 7,128,735 | B2 | 10/2006 | Weston |
| 7,144,390 | B1 | 12/2006 | Hannigan et al. |
| 7,153,312 | B1 | 12/2006 | Torrie et al. |
| 7,156,862 | B2 | 1/2007 | Jacobs et al. |
| 7,172,615 | B2 | 2/2007 | Morriss et al. |
| 7,189,238 | B2 | 3/2007 | Lombardo et al. |
| 7,196,054 | B1 | 3/2007 | Drohan et al. |
| 7,198,046 | B1 | 4/2007 | Argenta |
| 7,216,651 | B2 | 5/2007 | Argenta et al. |
| D544,092 | S | 6/2007 | Lewis |
| 7,262,174 | B2 | 8/2007 | Jiang et al. |
| 7,279,612 | B1 | 10/2007 | Heaton et al. |
| 7,315,183 | B2 | 1/2008 | Hinterscher |
| 7,351,250 | B2 | 4/2008 | Zamierowski |
| 7,361,184 | B2 | 4/2008 | Joshi |
| 7,367,342 | B2 | 5/2008 | Butler |
| 7,381,211 | B2 | 6/2008 | Zamierowski |
| 7,381,859 | B2 | 6/2008 | Hunt et al. |
| 7,413,571 | B2 | 8/2008 | Zamierowski |
| 7,438,705 | B2 | 10/2008 | Karpowicz et al. |
| 7,494,482 | B2 | 2/2009 | Orgill et al. |
| 7,534,240 | B1 | 5/2009 | Johnson |
| 7,540,848 | B2 | 6/2009 | Hannigan et al. |
| 7,553,306 | B1 | 6/2009 | Hunt et al. |
| 7,553,923 | B2 | 6/2009 | Williams et al. |
| 7,569,742 | B2 | 8/2009 | Haggstrom et al. |
| 7,578,532 | B2 | 8/2009 | Schiebler |
| D602,583 | S | 10/2009 | Pidgeon et al. |
| 7,611,500 | B1 | 11/2009 | Lina et al. |
| 7,615,036 | B2 | 11/2009 | Joshi et al. |
| 7,618,382 | B2 | 11/2009 | Vogel et al. |
| 7,625,362 | B2 | 12/2009 | Boehringer |
| 7,645,269 | B2 | 1/2010 | Zamierowski |
| 7,651,484 | B2 | 1/2010 | Heaton et al. |
| 7,670,323 | B2 | 3/2010 | Hunt et al. |
| 7,678,102 | B1 | 3/2010 | Heaton |
| 7,683,667 | B2 | 3/2010 | Kim |
| 7,699,823 | B2 | 4/2010 | Haggstrom et al. |
| 7,699,830 | B2 | 4/2010 | Martin |
| 7,699,831 | B2 | 4/2010 | Bengtson et al. |
| 7,700,819 | B2 | 4/2010 | Ambrosio et al. |
| 7,708,724 | B2 | 5/2010 | Weston |
| 7,713,743 | B2 | 5/2010 | Villanueva et al. |
| 7,722,528 | B2 | 5/2010 | Arnal et al. |
| 7,723,560 | B2 | 5/2010 | Lockwood et al. |
| 7,754,937 | B2 | 7/2010 | Boehringer et al. |
| 7,776,028 | B2 | 8/2010 | Miller et al. |
| 7,777,522 | B2 | 8/2010 | Yang |
| 7,779,625 | B2 | 8/2010 | Joshi et al. |
| D625,801 | S | 10/2010 | Pidgeon et al. |
| 7,815,616 | B2 | 10/2010 | Boehringer et al. |
| 7,820,453 | B2 | 10/2010 | Heylen et al. |
| 7,846,141 | B2 | 12/2010 | Weston |
| 7,857,806 | B2 | 12/2010 | Karpowicz et al. |
| 7,892,181 | B2 | 2/2011 | Christensen et al. |
| 7,896,856 | B2 | 3/2011 | Petrosenko et al. |
| 7,909,805 | B2 | 3/2011 | Weston |
| 7,931,774 | B2 | 4/2011 | Hall et al. |
| 7,942,866 | B2 | 5/2011 | Radl et al. |
| 7,951,124 | B2 | 5/2011 | Boehringer et al. |
| 7,964,766 | B2 | 6/2011 | Blott et al. |
| 7,976,519 | B2 | 7/2011 | Bubb et al. |
| 7,976,524 | B2 | 7/2011 | Kudo et al. |
| 7,981,098 | B2 | 7/2011 | Boehringer et al. |
| 8,030,534 | B2 | 10/2011 | Radl et al. |
| 8,057,447 | B2 | 11/2011 | Olson et al. |
| 8,062,272 | B2 | 11/2011 | Weston |
| 8,062,331 | B2 | 11/2011 | Zamierowski |
| 8,067,662 | B2 | 11/2011 | Aali et al. |
| 8,070,773 | B2 | 12/2011 | Zamierowski |
| 8,080,702 | B2 | 12/2011 | Blott et al. |
| 8,100,887 | B2 | 1/2012 | Weston et al. |
| 8,114,126 | B2 | 2/2012 | Heaton et al. |
| 8,123,781 | B2 | 2/2012 | Zamierowski |
| 8,128,615 | B2 | 3/2012 | Blott et al. |
| 8,129,580 | B2 | 3/2012 | Wilkes et al. |
| 8,142,419 | B2 | 3/2012 | Heaton et al. |
| 8,162,909 | B2 | 4/2012 | Blott et al. |
| 8,172,816 | B2 | 5/2012 | Kazala, Jr. et al. |
| 8,182,413 | B2 | 5/2012 | Browning |
| 8,187,237 | B2 * | 5/2012 | Seegert ............... A61M 1/0088 604/304 |
| 8,188,331 | B2 | 5/2012 | Barta et al. |
| 8,192,409 | B2 | 6/2012 | Hardman et al. |
| 8,197,467 | B2 | 6/2012 | Heaton et al. |
| 8,207,392 | B2 | 6/2012 | Haggstrom et al. |
| 8,235,955 | B2 | 8/2012 | Blott et al. |
| 8,246,590 | B2 | 8/2012 | Hu et al. |
| 8,257,328 | B2 | 9/2012 | Augustine et al. |
| 8,273,105 | B2 | 9/2012 | Cohen et al. |
| 8,328,776 | B2 | 12/2012 | Kelch et al. |
| 8,337,411 | B2 | 12/2012 | Nishtala et al. |
| 8,353,931 | B2 | 1/2013 | Stopek et al. |
| 8,357,131 | B2 | 1/2013 | Olson |
| 8,376,972 | B2 | 2/2013 | Fleischmann |
| 8,399,730 | B2 | 3/2013 | Kazala, Jr. et al. |
| 8,430,867 | B2 | 4/2013 | Robinson et al. |
| 8,444,392 | B2 | 5/2013 | Turner et al. |
| 8,447,375 | B2 | 5/2013 | Shuler |
| 8,454,990 | B2 | 6/2013 | Canada et al. |
| 8,460,255 | B2 * | 6/2013 | Joshi .................. A61M 1/0031 602/42 |
| 8,460,257 | B2 | 6/2013 | Locke et al. |
| 8,481,804 | B2 | 7/2013 | Timothy |
| 8,486,032 | B2 | 7/2013 | Seegert et al. |
| 8,500,704 | B2 | 8/2013 | Boehringer et al. |
| 8,500,776 | B2 | 8/2013 | Ebner |
| 8,523,832 | B2 | 9/2013 | Seegert |
| 8,535,296 | B2 | 9/2013 | Blott et al. |
| 8,608,776 | B2 | 12/2013 | Malla et al. |
| 8,622,981 | B2 | 1/2014 | Hartwell et al. |
| 8,632,523 | B2 | 1/2014 | Eriksson et al. |
| 8,673,992 | B2 | 3/2014 | Eckstein et al. |
| 8,679,080 | B2 | 3/2014 | Kazala, Jr. et al. |

(56) References Cited

U.S. PATENT DOCUMENTS

| | | |
|---|---|---|
| 8,679,153 B2 | 3/2014 | Dennis |
| 8,680,360 B2 | 3/2014 | Greener et al. |
| 8,708,984 B2 | 4/2014 | Robinson et al. |
| 8,721,629 B2 | 5/2014 | Hardman et al. |
| 8,746,662 B2 | 6/2014 | Poppe |
| 8,747,375 B2 | 6/2014 | Barta et al. |
| 8,764,732 B2 | 7/2014 | Hartwell |
| 8,791,315 B2 | 7/2014 | Lattimore et al. |
| 8,791,316 B2 | 7/2014 | Greener |
| 8,802,916 B2 | 8/2014 | Griffey et al. |
| 8,821,535 B2 | 9/2014 | Greener |
| 8,843,327 B2 | 9/2014 | Vernon-Harcourt et al. |
| 8,945,030 B2 | 2/2015 | Weston |
| 9,044,579 B2 | 6/2015 | Blott et al. |
| 9,050,398 B2 | 6/2015 | Armstrong et al. |
| 9,061,095 B2 | 6/2015 | Adie et al. |
| 9,180,231 B2 | 11/2015 | Greener |
| 9,220,822 B2 | 12/2015 | Hartwell et al. |
| 9,408,755 B2 | 8/2016 | Larsson et al. |
| 9,421,132 B2 | 8/2016 | Dunn |
| 9,555,170 B2 | 1/2017 | Fleischmann |
| 9,655,807 B2 | 5/2017 | Locke et al. |
| 9,849,023 B2 | 12/2017 | Hall et al. |
| 2001/0029956 A1 | 10/2001 | Argenta |
| 2001/0034499 A1* | 10/2001 | Sessions ............ A61F 13/00021 602/46 |
| 2002/0022861 A1 | 2/2002 | Jacobs et al. |
| 2002/0077661 A1 | 6/2002 | Saadat |
| 2002/0161346 A1 | 10/2002 | Lockwood et al. |
| 2003/0065360 A1 | 4/2003 | Jacobs et al. |
| 2003/0220660 A1 | 11/2003 | Kortenbach et al. |
| 2004/0006319 A1 | 1/2004 | Lina et al. |
| 2004/0010275 A1 | 1/2004 | Jacobs et al. |
| 2004/0054346 A1 | 3/2004 | Zhu et al. |
| 2004/0064132 A1 | 4/2004 | Boehringer et al. |
| 2004/0147465 A1 | 7/2004 | Jiang et al. |
| 2004/0162512 A1 | 8/2004 | Liedtke et al. |
| 2004/0267312 A1 | 12/2004 | Kanner et al. |
| 2005/0119694 A1 | 6/2005 | Jacobs et al. |
| 2005/0142331 A1 | 6/2005 | Anderson et al. |
| 2005/0182445 A1 | 8/2005 | Zamierowski |
| 2005/0222613 A1 | 10/2005 | Ryan |
| 2005/0258887 A1 | 11/2005 | Ito |
| 2005/0267424 A1 | 12/2005 | Eriksson et al. |
| 2006/0020269 A1* | 1/2006 | Cheng ............ A61B 17/22031 606/113 |
| 2006/0058842 A1 | 3/2006 | Wilke et al. |
| 2006/0064124 A1 | 3/2006 | Zhu et al. |
| 2006/0069357 A1 | 3/2006 | Marasco |
| 2006/0079599 A1 | 4/2006 | Arthur |
| 2006/0135921 A1 | 6/2006 | Wiercinski et al. |
| 2006/0213527 A1 | 9/2006 | Argenta et al. |
| 2006/0257457 A1 | 11/2006 | Gorman et al. |
| 2006/0259074 A1 | 11/2006 | Kelleher et al. |
| 2006/0271018 A1 | 11/2006 | Korf |
| 2007/0032755 A1 | 2/2007 | Walsh |
| 2007/0038172 A1 | 2/2007 | Zamierowski |
| 2007/0052144 A1 | 3/2007 | Knirck et al. |
| 2007/0118096 A1 | 5/2007 | Smith et al. |
| 2007/0123816 A1 | 5/2007 | Zhu et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0219513 A1 | 9/2007 | Lina et al. |
| 2007/0282309 A1 | 12/2007 | Bengtson et al. |
| 2007/0282374 A1 | 12/2007 | Soaard et al. |
| 2007/0299541 A1 | 12/2007 | Chernomorsky et al. |
| 2008/0041401 A1 | 2/2008 | Casola et al. |
| 2008/0108977 A1 | 5/2008 | Heaton et al. |
| 2008/0167593 A1 | 7/2008 | Fleischmann |
| 2008/0177253 A1 | 7/2008 | Boehringer et al. |
| 2008/0275409 A1 | 11/2008 | Kane et al. |
| 2008/0287973 A1 | 11/2008 | Aster et al. |
| 2009/0005716 A1 | 1/2009 | Abuzaina et al. |
| 2009/0005744 A1 | 1/2009 | Karpowicz et al. |
| 2009/0018578 A1 | 1/2009 | Wilke et al. |
| 2009/0018579 A1 | 1/2009 | Wilke et al. |
| 2009/0043268 A1 | 2/2009 | Eddy et al. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0131888 A1 | 5/2009 | Joshi |
| 2009/0137973 A1 | 5/2009 | Karpowicz et al. |
| 2009/0204423 A1 | 8/2009 | DeGheest et al. |
| 2009/0227938 A1 | 9/2009 | Fasching et al. |
| 2009/0246238 A1 | 10/2009 | Gorman et al. |
| 2009/0259203 A1 | 10/2009 | Hu et al. |
| 2009/0299303 A1 | 12/2009 | Seegert |
| 2010/0022972 A1 | 1/2010 | Lina et al. |
| 2010/0022990 A1 | 1/2010 | Karpowicz et al. |
| 2010/0028407 A1 | 2/2010 | Del Priore et al. |
| 2010/0030132 A1 | 2/2010 | Niezgoda et al. |
| 2010/0036333 A1 | 2/2010 | Schenk, III et al. |
| 2010/0047324 A1 | 2/2010 | Fritz et al. |
| 2010/0081983 A1 | 4/2010 | Zocher et al. |
| 2010/0100063 A1 | 4/2010 | Joshi et al. |
| 2010/0106184 A1 | 4/2010 | Coward et al. |
| 2010/0121286 A1 | 5/2010 | Locke et al. |
| 2010/0121287 A1 | 5/2010 | Smith et al. |
| 2010/0125233 A1* | 5/2010 | Edward ............... A61M 1/0088 602/42 |
| 2010/0137775 A1 | 6/2010 | Hu et al. |
| 2010/0137890 A1 | 6/2010 | Martinez et al. |
| 2010/0150991 A1 | 6/2010 | Bernstein |
| 2010/0160874 A1 | 6/2010 | Robinson et al. |
| 2010/0160876 A1 | 6/2010 | Robinson et al. |
| 2010/0160901 A1 | 6/2010 | Hu et al. |
| 2010/0179515 A1 | 7/2010 | Swain et al. |
| 2010/0198128 A1 | 8/2010 | Turnlund et al. |
| 2010/0211030 A1 | 8/2010 | Turner et al. |
| 2010/0256672 A1 | 10/2010 | Weinberg et al. |
| 2010/0262126 A1 | 10/2010 | Hu et al. |
| 2010/0280468 A1 | 11/2010 | Haggstrom et al. |
| 2010/0292717 A1 | 11/2010 | Petier-Puchner et al. |
| 2011/0004173 A1 | 1/2011 | Hu et al. |
| 2011/0009838 A1 | 1/2011 | Greener |
| 2011/0015594 A1 | 1/2011 | Hu et al. |
| 2011/0021965 A1 | 1/2011 | Karp et al. |
| 2011/0022082 A1 | 1/2011 | Burke et al. |
| 2011/0054283 A1 | 3/2011 | Shuler |
| 2011/0060204 A1 | 3/2011 | Weston |
| 2011/0066096 A1 | 3/2011 | Svedman |
| 2011/0077605 A1 | 3/2011 | Karpowicz et al. |
| 2011/0082480 A1 | 4/2011 | Viola |
| 2011/0105963 A1 | 5/2011 | Hu et al. |
| 2011/0106026 A1 | 5/2011 | Wu et al. |
| 2011/0110996 A1 | 5/2011 | Schoenberger et al. |
| 2011/0112458 A1 | 5/2011 | Holm et al. |
| 2011/0130774 A1 | 6/2011 | Criscuolo et al. |
| 2011/0172760 A1 | 7/2011 | Anderson |
| 2011/0178451 A1 | 7/2011 | Robinson et al. |
| 2011/0224631 A1 | 9/2011 | Simmons |
| 2011/0224632 A1 | 9/2011 | Zimitsky et al. |
| 2011/0224634 A1 | 9/2011 | Locke et al. |
| 2011/0236460 A1 | 9/2011 | Stopek et al. |
| 2011/0238095 A1 | 9/2011 | Browning |
| 2011/0238110 A1 | 9/2011 | Wilke et al. |
| 2011/0264138 A1 | 10/2011 | Avelar et al. |
| 2011/0282136 A1 | 11/2011 | Brownina |
| 2011/0282309 A1 | 11/2011 | Adie et al. |
| 2011/0282310 A1 | 11/2011 | Boehringer et al. |
| 2012/0004631 A9 | 1/2012 | Hartwell |
| 2012/0010637 A1 | 1/2012 | Stopek et al. |
| 2012/0016321 A1 | 1/2012 | Wu et al. |
| 2012/0029449 A1 | 2/2012 | Khosrowshahi |
| 2012/0029455 A1 | 2/2012 | Perez-Foullerat et al. |
| 2012/0035560 A1 | 2/2012 | Eddy et al. |
| 2012/0059399 A1 | 3/2012 | Hoke et al. |
| 2012/0059412 A1 | 3/2012 | Fleischmann |
| 2012/0071841 A1 | 3/2012 | Bengtson |

(56) References Cited

U.S. PATENT DOCUMENTS

| | | |
|---|---|---|
| 2012/0083755 A1 | 4/2012 | Lina et al. |
| 2012/0109188 A1 | 5/2012 | Viola |
| 2012/0121556 A1 | 5/2012 | Fraser et al. |
| 2012/0130327 A1 | 5/2012 | Marquez Canada |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0144989 A1 | 6/2012 | De Plessis et al. |
| 2012/0150133 A1 | 6/2012 | Heaton et al. |
| 2012/0165764 A1 | 6/2012 | Allen et al. |
| 2012/0172926 A1 | 7/2012 | Hotter |
| 2012/0191054 A1 | 7/2012 | Kazala, Jr. et al. |
| 2012/0191132 A1 | 7/2012 | Sargeant |
| 2012/0197415 A1 | 8/2012 | Montanari et al. |
| 2012/0209226 A1 | 8/2012 | Simmons et al. |
| 2012/0209227 A1 | 8/2012 | Dunn |
| 2012/0253302 A1 | 10/2012 | Corley |
| 2012/0277773 A1 | 11/2012 | Sargeant et al. |
| 2013/0096518 A1 | 4/2013 | Hall |
| 2013/0131564 A1 | 5/2013 | Locke et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0253401 A1 | 9/2013 | Locke et al. |
| 2013/0331757 A1 | 12/2013 | Belson |
| 2014/0068914 A1 | 3/2014 | Coward et al. |
| 2014/0094730 A1 | 4/2014 | Greener |
| 2014/0163415 A1 | 6/2014 | Zaiken et al. |
| 2014/0180225 A1 | 6/2014 | Dunn |
| 2014/0194836 A1 | 7/2014 | Kazala, Jr. et al. |
| 2014/0194837 A1 | 7/2014 | Robinson et al. |
| 2014/0213994 A1 | 7/2014 | Hardman et al. |
| 2014/0228789 A1 | 8/2014 | Wilkes et al. |
| 2014/0249495 A1 | 9/2014 | Mumby |
| 2015/0025484 A1 | 1/2015 | Simmons et al. |
| 2015/0065968 A1 | 3/2015 | Sealy et al. |
| 2015/0112311 A1 | 4/2015 | Hammond et al. |
| 2015/0119837 A1 | 4/2015 | Thompson, Jr. et al. |
| 2015/0157758 A1 | 6/2015 | Blucher et al. |
| 2015/0159066 A1 | 6/2015 | Hartwell et al. |
| 2015/0174304 A1 | 6/2015 | Askem et al. |
| 2015/0196431 A1 | 7/2015 | Dunn |
| 2015/0320602 A1 | 11/2015 | Locke et al. |
| 2016/0022885 A1 | 1/2016 | Dunn et al. |
| 2016/0030646 A1 | 2/2016 | Hartwell et al. |
| 2016/0166744 A1 | 6/2016 | Hartwell |
| 2016/0287765 A1 | 10/2016 | Canner et al. |

FOREIGN PATENT DOCUMENTS

| | | |
|---|---|---|
| CN | 101208115 | 6/2008 |
| CN | 101257938 | 9/2008 |
| CN | 102256637 | 11/2011 |
| CN | 102781380 | 11/2012 |
| CN | 203408163 | 1/2014 |
| CN | 104736110 A | 6/2015 |
| DE | 2 949 920 | 3/1981 |
| DE | 10 2005 007016 | 8/2006 |
| EP | 1 320 342 | 6/2003 |
| EP | 2 279 016 | 2/2011 |
| EP | 2 366 721 | 9/2011 |
| EP | 2 368 523 | 9/2011 |
| EP | 2 404 626 | 1/2012 |
| EP | 2 341 955 | 12/2012 |
| EP | 2 529 767 | 12/2012 |
| EP | 2 567 682 | 3/2013 |
| EP | 2 567 717 | 3/2013 |
| EP | 2 594 299 | 5/2013 |
| EP | 2 601 984 A2 | 6/2013 |
| EP | 2 623 137 | 8/2013 |
| EP | 2 367 517 | 9/2013 |
| EP | 3 225 261 | 10/2017 |
| GB | 2389794 | 12/2003 |
| GB | 2423019 | 8/2006 |
| GB | 2489947 | 10/2012 |
| GB | 2496310 | 5/2013 |
| JP | H09-503923 | 4/1997 |
| JP | 2007-505678 | 3/2007 |
| JP | 2007-531567 | 11/2007 |
| JP | 2008-529618 | 8/2008 |
| JP | 2009-536851 | 10/2009 |
| JP | 2010-526597 | 8/2010 |
| JP | 2011-500170 | 1/2011 |
| JP | 2011-523575 | 8/2011 |
| JP | 2013-526938 | 6/2013 |
| RU | 1818103 | 5/1993 |
| RU | 62504 | 4/2007 |
| WO | WO 2001/085248 | 11/2001 |
| WO | WO 2001/89392 | 11/2001 |
| WO | WO 2002/05737 | 1/2002 |
| WO | WO 2003/003948 | 1/2003 |
| WO | WO 2004/018020 | 3/2004 |
| WO | WO 2004/037334 | 5/2004 |
| WO | WO 2005/046761 | 5/2005 |
| WO | WO 2005/105174 | 11/2005 |
| WO | WO 2006/046060 | 5/2006 |
| WO | WO 2006/087021 | 8/2006 |
| WO | WO 2007/030601 | 3/2007 |
| WO | WO 2007/133618 | 11/2007 |
| WO | WO 2008/039223 | 4/2008 |
| WO | WO 2008/064502 | 6/2008 |
| WO | WO 2008/091521 | 7/2008 |
| WO | WO 2008/104609 | 9/2008 |
| WO | WO 2009/019495 | 2/2009 |
| WO | WO 2009/071926 | 6/2009 |
| WO | WO 2009/071933 | 6/2009 |
| WO | WO 2009/112062 | 9/2009 |
| WO | WO 2009/112848 | 9/2009 |
| WO | WO 2009/114624 | 9/2009 |
| WO | WO 2009/156709 | 12/2009 |
| WO | WO 2010/033725 | 3/2010 |
| WO | WO 2010/051073 | 5/2010 |
| WO | WO 2010/059612 | 5/2010 |
| WO | WO 2010/075180 | 7/2010 |
| WO | WO 2010/078349 | 7/2010 |
| WO | WO 2010/092334 | 8/2010 |
| WO | WO 2010/097570 | 9/2010 |
| WO | WO 2010/075178 | 10/2010 |
| WO | WO 2010/147535 | 12/2010 |
| WO | WO 2011/023384 | 3/2011 |
| WO | WO 2011/087871 | 7/2011 |
| WO | WO 2011/091169 | 7/2011 |
| WO | WO 2011/106722 | 9/2011 |
| WO | WO 2011/135284 | 11/2011 |
| WO | WO 2011/135286 | 11/2011 |
| WO | WO 2011/135287 | 11/2011 |
| WO | WO 2011/137230 | 11/2011 |
| WO | WO 2011/144888 | 11/2011 |
| WO | WO 2012/021553 | 2/2012 |
| WO | WO 2012/038727 | 3/2012 |
| WO | WO 2012/069793 | 5/2012 |
| WO | WO 2012/069794 | 5/2012 |
| WO | WO 2012/082716 | 6/2012 |
| WO | WO 2012/082876 | 6/2012 |
| WO | WO 2012/106590 | 8/2012 |
| WO | WO 2012/112204 | 8/2012 |
| WO | WO 2012/136707 | 10/2012 |
| WO | WO 2012/142473 | 10/2012 |
| WO | WO 2012/156655 | 11/2012 |
| WO | WO 2012/168678 | 12/2012 |
| WO | WO 2013/007973 | 1/2013 |
| WO | WO 2013/012381 | 1/2013 |
| WO | WO 2013/043258 | 3/2013 |
| WO | WO 2013/071243 | 5/2013 |
| WO | WO 2013/074829 | 5/2013 |
| WO | WO 2013/076450 | 5/2013 |
| WO | WO 2014/013348 | 5/2013 |
| WO | WO 2013/079947 | 6/2013 |
| WO | WO 2013/175309 | 11/2013 |
| WO | WO 2013/175310 | 11/2013 |
| WO | WO 2014/014842 | 1/2014 |
| WO | WO 2014/014871 | 1/2014 |
| WO | WO 2014/014922 | 1/2014 |
| WO | WO 2014/024048 | 2/2014 |

(56) References Cited

FOREIGN PATENT DOCUMENTS

| WO | WO 2014/140578 | 9/2014 |
| WO | WO 2014/158526 | 10/2014 |
| WO | WO 2014/165275 | 10/2014 |
| WO | WO 2015/008054 | 1/2015 |
| WO | WO 2015/061352 | 4/2015 |
| WO | WO 2015/109359 | 7/2015 |
| WO | WO 2015/110409 | 7/2015 |
| WO | WO 2015/110410 | 7/2015 |
| WO | WO 2016/176513 | 11/2016 |

OTHER PUBLICATIONS

Merriam-Webster Dictionary, definition of "throughout", https://www.merriam-webster.com/dictionary/throughout.*
U.S. Appl. No. 14/402,976, dated Nov. 21, 2014, Dodd et al.
Hougaard, et al.: "The open abdomen: temporary closure with a modified negative pressure therapy technique," International Wound Journal, 2014 ISSN 1742-4801, pp. 13-16.
International Search Report and Written Opinion re PCT/IB2013/001555, dated Sep. 3, 2013.
Kapischke, M. et al., "Self-fixating mesh for the Lichtenstein procedure-a prestudy", Langenbecks Arch Surg (2010), 395 p. 317-322.
International Preliminary Report on Patentability, re PCT/IB2013/001555, dated Nov. 25, 2014.
Definition of "3D Printer", American Heritage Dictionary of the English Language, Fifth Edition, 2016, accessed Feb. 22, 2018, in 1 page. URL: https://www.thefreedictionary.co.
Definition of "Oculiform", Webster's Revised Unabridged Dictionary, 1913, accessed from The Free Dictionary on May 30, 2018, in 1 page. URL: https://www.thefreedictionary.com/Oculiform.

* cited by examiner

Variable Density Composite

Tubes within tubes positioned at the top of a wound filler. Prevents the filler from moving vertically but tubes will slide into each other allowing horizontal movement. Straws could be single with a concertina effect in the middle.

Stiffener for drape, does not allow drape to sag under vacuum and therefore filler does not compress vertically only laterally.

Silicone contact layer, non-adhesive to prevent adhesion to stomach wall, on the base of the filler. Or greater skinning on base of filler Use of NPWT at wound edge to get full contact for a closure mechanism (i.e. use this to engage wound edges then have for example a shoe lace system to pull wound edges in).

Provide "pinking shears" to cut filler outer perimeter to give protrusions and aid fixation

DEVICES AND METHODS FOR TREATING AND CLOSING WOUNDS WITH NEGATIVE PRESSURE

CROSS-REFERENCE TO RELATED APPLICATIONS

This application is a national stage application of International Patent Application No. PCT/IB2013/001555, filed on May 23, 2013, which claims the benefit of U.S. Provisional Application Nos. 61/651,483, filed May 24, 2012, entitled DEVICES AND METHODS FOR TREATING AND CLOSING WOUNDS WITH NEGATIVE PRESSURE, and 61/782,270, filed Mar. 14, 2013, entitled DEVICES AND METHODS FOR TREATING AND CLOSING WOUNDS WITH NEGATIVE PRESSURE, the contents of which are hereby incorporated by reference in their entireties as if fully set forth herein. The benefit of priority to the foregoing applications is claimed under the appropriate legal basis including, without limitation, under 35 U.S.C. § 119(e).

BACKGROUND OF THE INVENTION

Field of the Invention

Embodiments described herein relate to devices and methods that can be used to treat a wound with negative pressure. Particular embodiments can also be useful to aid in wound closure, for example in abdominal wounds.

Description of the Related Art

In the prior art, application of negative pressure may sometimes exert an outward force upon the wound margins due to the atmospheric pressure compressing the wound filler downward and outward against the margins of the wound. This downward compression of the wound filler slows the healing process and slows or prevents wound closure. Accordingly, there is a need to provide for an improved apparatus, method, and system for the treatment and closure of wounds.

SUMMARY OF THE INVENTION

Generally, the embodiments described herein can be used to assist in the treatment of wounds with negative pressure. The embodiments can be particularly useful in treating large wounds, such as abdominal wounds, where closure and approximation of the wound edges is challenging. By limiting the amount of vertical pressure applied to the wound filler, by enhancing the horizontal collapse of the wound filler, and by enhancing attachment of the wound filler to the wound margins, together with additional details described herein, improved wound closure can be obtained.

In some embodiments, a wound filler for use in treating a wound with negative pressure comprises:
 a porous filling material;
 a plurality of vertically extending members configured to extend vertically when the wound filler is positioned within a wound bed, the vertically extending members being made of a more rigid material than the porous wound filling material; and
 wherein upon application of negative pressure to the wound filler, the wound filler is configured to contract horizontally with the vertically extending members reducing vertical movement of the wound filler.

In certain embodiments, the vertically extending members can be struts, slabs, columns or tiles. In some embodiments, the vertically extending members of any of the aforementioned wound filler embodiments are elongate members configured to extend lengthwise across a wound bed and are aligned parallel to one another. In particular embodiments, the porous wound filling material of any of the aforementioned wound filler embodiments can surround the vertically extending members. In some embodiments, the porous wound filling material of any of the aforementioned wound filler embodiments can extend between the vertically extending members. In particular embodiments, the porous wound filling material of any of the aforementioned wound filler embodiments can comprise a plurality of slits or areas in which denser or more rigid struts or slabs are inserted.

In particular embodiments, the wound fillers of any of the aforementioned embodiments can include flexible material positioned between the vertically extending members to allow compression of the vertically extending members towards each other in a horizontal plane when the wound filler is positioned within a wound bed and is placed under negative pressure. In some embodiments, the vertically extending members of any of the aforementioned wound filler embodiments can be adhered to the porous wound filling material.

In some embodiments, one or more draw strings or cords can extend through the wound filler such that pulling of the draw strings causes contraction of the wound filler in a horizontal plane.

In certain embodiments, a negative pressure wound therapy system comprises a wound filler such as those described herein and a wound cover configured to be placed over the wound filler. In certain embodiments, the negative pressure wound therapy system described above further includes a connection for connecting the wound cover to a source of negative pressure. In some embodiments, the aforementioned negative pressure wound therapy system further comprises a negative pressure source configured to be connected to the wound cover to provide negative pressure to the wound filler when placed within the wound bed.

In some embodiments, a method of treating a wound comprises:
 positioning a wound filler of any one of the previously described embodiments into a wound bed;
 covering the wound filler with a wound cover; and
 applying negative pressure to the wound cover, wherein the application of negative pressure causes the wound filler to contract horizontally with the vertically extending members reducing vertical movement of the wound filler.

Other embodiments of wound closure devices, stabilizing structures and associated apparatuses are described below.

BRIEF DESCRIPTION OF THE DRAWINGS

Other features and advantages of the present invention will be apparent from the following detailed description of the invention, taken in conjunction with the accompanying drawings of which.

DETAILED DESCRIPTION OF THE PREFERRED EMBODIMENTS

Figure 1:
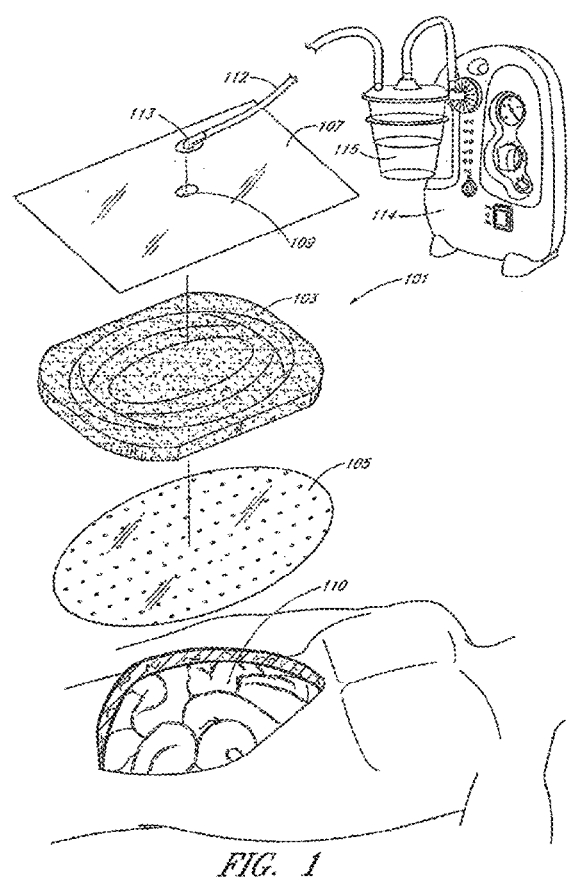
FIG. 1 illustrates one embodiment of a negative pressure wound therapy system.

Embodiments of wound fillers and other wound treatment apparatuses and methods that may be utilized with and/or that may provide further details regarding the embodiments described below are found in U.S. Provisional Application No. 61/651,483, filed May 24, 2012, the entirety of which is hereby incorporated by reference and portions of which are included below in the section titled "Other Negative Pressure Therapy Apparatuses, Dressings, Wound Fillers, and Methods."

Various embodiments that can be used for the treatment of wounds will now be described with references to the following figures and description which follow. It will be of course understood that various omissions, substitutions, and changes in the form and details of the embodiments illustrated can be made without departing from the spirit of the disclosure. Additionally, the various features and processes described herein can be used independently of one another, or can be combined in various ways. All possible combinations and subcombinations are intended to fall within the scope of this disclosure. Many of the embodiments described herein include similar components, and as such, these similar components can be interchanged in different embodiments.

Embodiments disclosed herein relate to apparatuses and methods of treating a wound with reduced pressure, including pump and wound dressing components and apparatuses. Generally, the embodiments including the wound fillers described herein may be used in combination with a negative pressure system comprising a drape or wound cover placed over the filler. A vacuum source, such as a pump, may be connected to the cover, for example, through one or more tubes connected to an aperture or port made in or under the cover. The apparatuses and components comprising the wound overlay and packing materials, if any, are sometimes collectively referred to herein as dressings. Reference is made to the following applications, which are hereby incorporated by reference in their entireties: U.S. application Ser. No. 12/886,088, titled "SYSTEMS AND METHODS FOR USING NEGATIVE PRESSURE WOUND THERAPY TO MANAGE OPEN ABDOMINAL WOUNDS", published as US 2011/0213287 on Sep. 1, 2011; and U.S. application Ser. No. 13/092,042, titled "WOUND DRESSING AND METHOD OF USE", published as US 2011/0282309 on Nov. 17, 2011.

It will be appreciated that throughout this specification reference is made to a wound or wounds. It is to be understood that the term wound is to be broadly construed and encompasses open and closed wounds in which skin is torn, cut or punctured, or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the negative pressure treatment system described herein can be particularly suited for incisional wounds that exude a small amount of wound exudate.

As is used herein, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −20 mmHg and −200 mmHg. Note that these pressures are relative to normal ambient atmospheric pressure. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even 150 mmHg, can be supplied by the negative pressure apparatus.

As used herein, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal," and "lateral" can also be used to describe the wound fillers or other devices described throughout this specification. When describing these wound fillers or devices, these terms should not be construed to require that the structures or devices necessarily be placed into a wound in a certain orientation, though in certain embodiments, it may be preferable to do so.

As used herein, the term "fill material" comprises, in a non-limiting manner: porous wound filler materials and flexible materials. As used herein, compressible materials are included within the scope of flexible materials.

Turning to FIG. 1, treatment of a wound with negative pressure in certain embodiments uses a negative pressure treatment system 101 as illustrated schematically here. In this embodiment, a wound site 110, illustrated here as an abdominal wound site, may benefit from treatment with negative pressure. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound site 110 can be beneficial to a patient.

Accordingly, certain embodiments provide for a wound contact layer 105 to be placed over the wound site 110. Preferably, the wound contact layer 105 can be a thin, flexible material which will not adhere to the wound site or the exposed viscera in close proximity. For example, polymers such as polyurethane, polyethylene, polytetrafluoroethylene, or blends thereof may be used. In one embodiment, the wound contact layer is permeable. For example, the wound contact layer 105 can be provided with openings, such as holes, slits, or channels, to allow the removal of fluids from the wound site 110 or the transmittal of negative pressure to the wound site 110.

Certain embodiments of the negative pressure treatment system 101 may also use a porous wound filler 103, which can be disposed over the wound contact layer 105. This pad 103 can be constructed from a porous material, for example foam, that is soft, resiliently flexible, and generally conformable to the wound site 110. Such a foam can include an open-celled and reticulated foam made, for example, of a polymer. Suitable foams include foams composed of, for example, polyurethane, silicone, and polyvinyl alcohol. Preferably, this pad 103 can channel wound exudate and other fluids through itself when negative pressure is applied to the wound. Some pads 103 may include preformed channels or openings for such purposes. In certain embodiments, the pad 103 may have a thickness between about one inch and about two inches. The pad may also have a length of between about 16 and 17 inches, and a width of between about 11 and 12 inches. In other embodiments, the thickness, width, and/or length can have other suitable values. Other embodiments of wound fillers that may be used in place of or in addition to the pad 103 are discussed in further detail below.

Preferably, a drape 107 is used to seal the wound site 110. The drape 107 can be at least partially liquid impermeable, such that at least a partial negative pressure may be maintained at the wound site. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling the drape 107; in some embodiments, the release layer may be composed of multiple sections.

The negative pressure system 101 can be connected to a source of negative pressure, for example a pump 114. One example of a suitable pump is the Renasys EZ pump available from Smith & Nephew. The drape 107 may be connected to the source of negative pressure 114 via a conduit 112. The conduit 112 may be connected to a port 113 situated over an aperture 109 in the drape 107, or else the conduit 112 may be connected directly through the aperture 109 without the use of a port. In a further alternative, the conduit may pass underneath the drape and extend from a side of the drape. U.S. Pat. No. 7,524,315 discloses other similar aspects of negative pressure systems and is hereby incorporated by reference in its entirety and should be considered a part of this specification.

In many applications, a container or other storage unit 115 may be interposed between the source of negative pressure 114 and the conduit 112 so as to permit wound exudate and other fluids removed from the wound site to be stored without entering the source of negative pressure. Certain types of negative pressure sources—for example, peristaltic pumps—may also permit a container 115 to be placed after the pump 114. Some embodiments may also use a filter to prevent fluids, aerosols, and other microbial contaminants from leaving the container 115 and/or entering the source of negative pressure 114. Further embodiments may also include a shut-off valve or occluding hydrophobic and/or oleophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister.

Figure 2A:
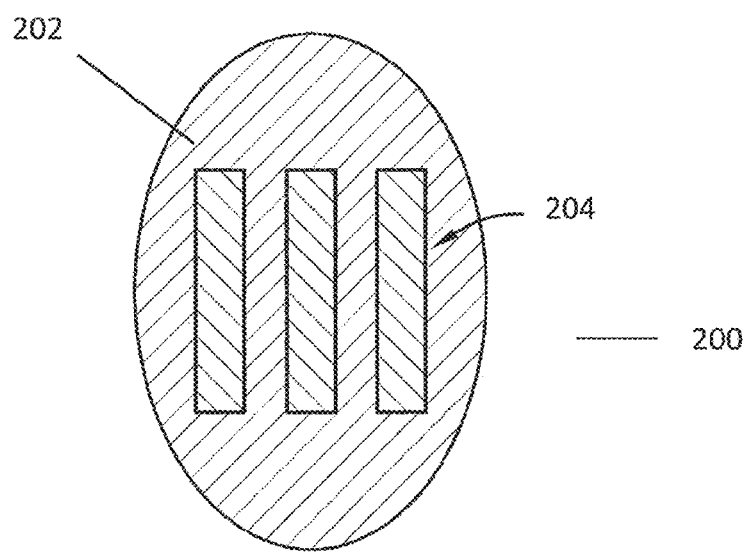
FIG. 2A is a cross-sectional view of one embodiment of a wound filler taken through a horizontal plane.

FIGS. 2A-2E illustrate embodiments of a wound filler 200 that may be used in the system described above comprising fill material 202 and extending members 204. In some preferred embodiments, the fill material is a porous wound filler material such as described above. In certain preferred embodiments, the fill material 202 is flexible. As shown in a horizontal cross-section in FIG. 2A, the wound filler 200 may include a plurality of extending members 204 contained within an oval-shaped fill material 202. It will be appreciated that the fill material 202 can have other shapes, such as rectangular or square, and that the shape shown in FIG. 2A may simply result from the filler being cut by a health practitioner to an appropriate size. The wound filler as shown in FIG. 2A is shown with an outer dimension sized to fit within an oval-shaped wound when the wound is viewed from above.

In some embodiments, the extending members 204 are denser than the fill material 202. In some embodiments, the extending members 204 are between 1 to 2 times, between 2 to 4 times, between 4 to 6 times, between 6 to 8 times, or 8 times or more dense than the fill material. In certain embodiments, the extending members 204 are more rigid than the fill material 202. In some embodiments, the extending members are between 1 to 2 times, between 2 to 4 times, between 4 to 6 times, between 6 to 8 times, or 8 times or more rigid than the porous wound filling material.

In certain preferable embodiments, and as also shown in FIGS. 2B-2E, the extending members 204 are elongate members that extend vertically when the wound filler 200 is positioned within a wound bed. In particular embodiments, as shown in FIG. 2A, the extending members 204 are elongate members that may also extend horizontally across a portion or the entire longitudinal length of the wound filler when the wound filler 200 is positioned within a wound bed. In some embodiments, the extending members 204 are sheets that may have parallel faces, while in other embodiments, the extending members 204 may comprise struts, slabs, columns, or tiles. In other embodiments, the extending members 204 extend at an angle from the horizontal or vertical plane of the wound.

The extending members 204 may be parallel or substantially parallel to one another, and may be spaced apart 204 either equally or unequally. In horizontal cross-section as shown in FIG. 2A, each of the extending members may have the same thicknesses, or alternatively, they may have different thicknesses. In vertical cross-section as shown in FIGS. 2B-2E, the extending members may have the same vertical height or length, or may have different vertical heights or lengths. The dimensions of the wound filler, and particularly the horizontal length and the vertical height of the extending members as well as the number of extending members, may depend on the size to which the filler material is cut by the health practitioner. In the embodiments shown, the extending members may have a rectangular cross-section in both horizontal and vertical cross-section, where the horizontal length is greater than the thickness, and the vertical height is greater than the thickness. In some embodiments, the extending members may comprise sheets. In one embodiment, the wound filler is configured to be placed in a wound such that the horizontal length of the extending members is parallel or generally parallel to the longitudinal length of the wound, and the thickness dimension of the extending members extend in the lateral direction.

In some embodiments, as shown in FIG. 2A, the fill material 202 contains slits or areas for the insertion of extending members 204. In some embodiments, the extending members 204 can be inserted after the wound filler 200 has been placed in the wound. In other embodiments, the extending members 204 are placed within the wound filler prior to insertion into the wound. In some embodiments, the slits or areas for insertion can be made after the wound filler 200 has been placed in the wound. In certain embodiments, the slits or areas for insertion are made before the wound filler is placed in the wound. In embodiments where the fill material 202 contains slits or areas for insertion of extending members, the slits may be open to a top surface and/or a bottom surface of the fill material to allow the extending members to be vertically inserted. As shown in FIG. 2A, the horizontal length of the extending members may be shorter than a horizontal dimension of the fill material 202, such that the extending members 204 are fully surrounded by the fill material 202 in a horizontal plane. In some embodiments, the extending members may be attached to the fill material, such as with adhesive, barbs, Velcro™ or other attachment mechanisms. In other embodiments, the extending members may simply be inserted into the slits or areas for insertion of the fill material and be connected by friction, an interference fit, a slight expansion of the extending members, or other mechanical forces.

Figure 2B:
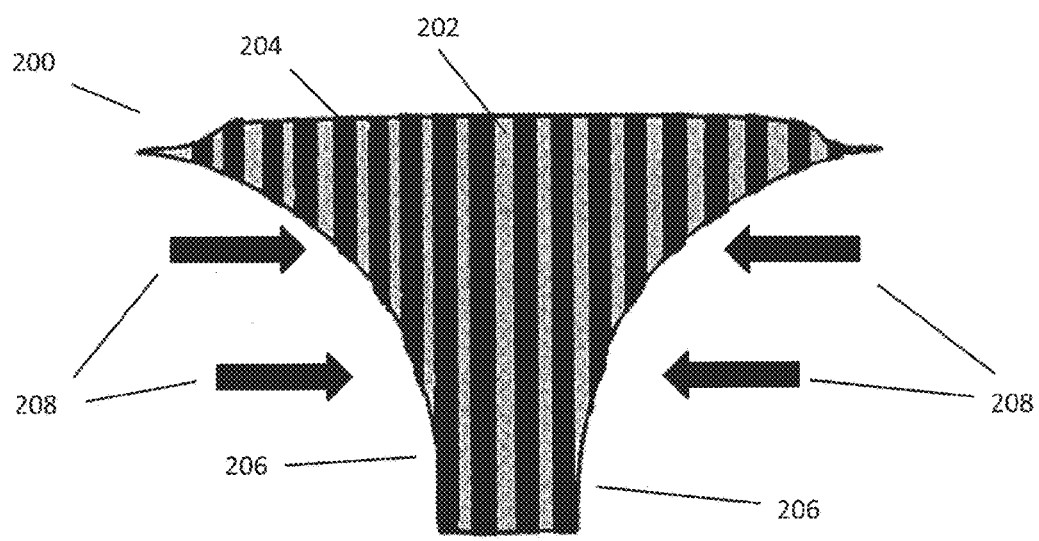
FIG. 2B is a cross-sectional view of a wound with a wound filler positioned therein.
Figure 2C:
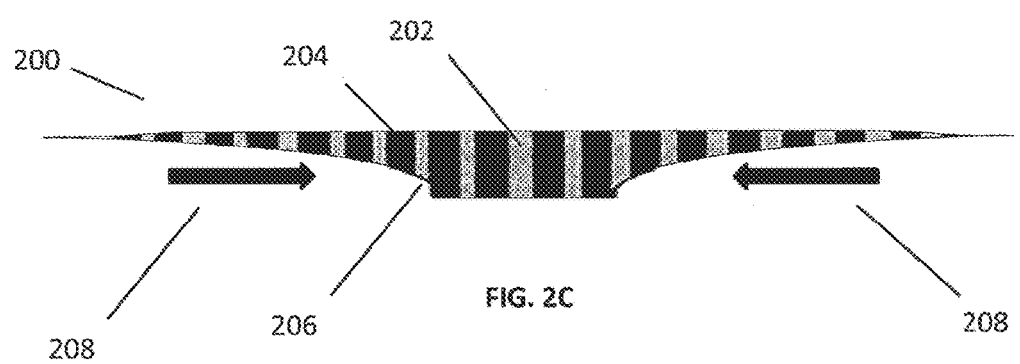
FIG. 2C is a cross-sectional view of another type of wound with a wound filler positioned therein.
Figure 2D:
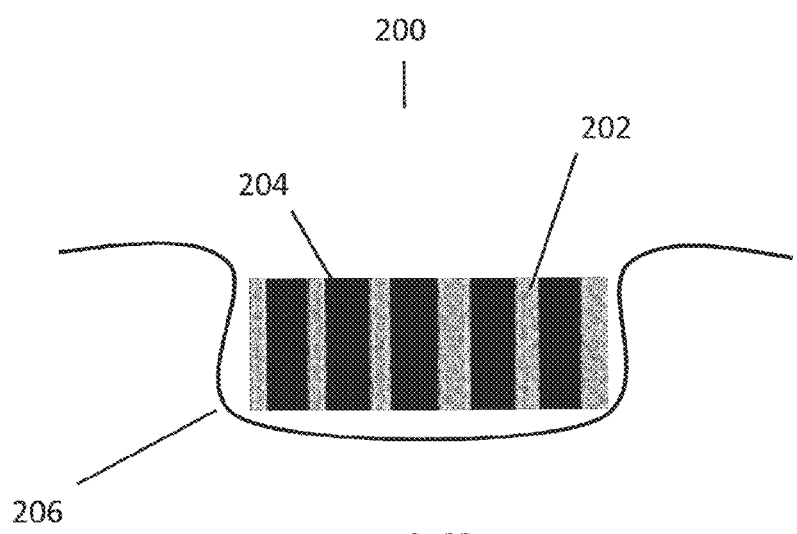
FIG. 2D is a cross-sectional view of another type of wound with a wound filler positioned therein.

As shown in FIGS. 2B-2D, the extending members can be vertical when positioned within a wound. FIG. 2B illustrates a side or vertical cross-sectional view of an embodiment of a wound filler 200 positioned within a wound 206, with vertical extending members 204 and fill material 202. The extending members may be similar to those shown in FIG. 2A, or they may consist of alternate slabs of material that may be parallel or substantially parallel to one another. Thus, in some embodiments, instead of having extending members inserted or surrounded by fill material, the extending members and fill material can comprise multiple layers, sheets or slabs alternatingly stacked and adhered together to form a hybrid laminate. For example, a layer of more flexible or compressible wound filler (e.g., foam) may alternatingly be stacked with layers of more rigid wound filler. It will be appreciated that even in such a configuration, further layers of porous material such as foam may be placed above and below the wound filler 200, or the entire wound filler may be surrounded by a porous material such as foam.

In some embodiments, upon application of negative pressure to the wound filler 200, for example, using the system previously described with respect to FIG. 1, the wound filler 200 is configured to contract horizontally 208 with the vertical extending members 204 reducing vertical movement of the wound filler 200. The fill material 202 extends between the plurality of vertically extending members 204 and the fill material and the vertically extending members may be adhered together. As shown in FIG. 2B, as negative pressure is applied to close the wound 206, the fill material 202 between the vertically extending members 204 may desirably compress so that the vertically extending members come closer together as the wound closes.

FIG. 2C illustrates a cross-sectional view of an embodiment of a wound filler 200 in a shallow wound 206, comprising a fill material 202 with spaced apart areas in which a plurality of extending members 204 are located. In a similar manner to the embodiments described in FIGS. 2A-2B, the wound filler is configured to compress horizontally 208, but vertical compression is limited.

FIG. 2D illustrates another cross-sectional view of an embodiment of a wound filler 200 for use in a wound 206, similar to the embodiments described in FIGS. 2A-2C, comprising denser material 204 alternating with less dense material 202 similar to the embodiments described above. In the embodiment of FIG. 2D, the wound filler 200 may have or be cut to a shape where the upper and lower surfaces of the wound filler are parallel or substantially parallel. As illustrated, the extending members of denser material 204 may have the same vertical height.

Figure 2E:
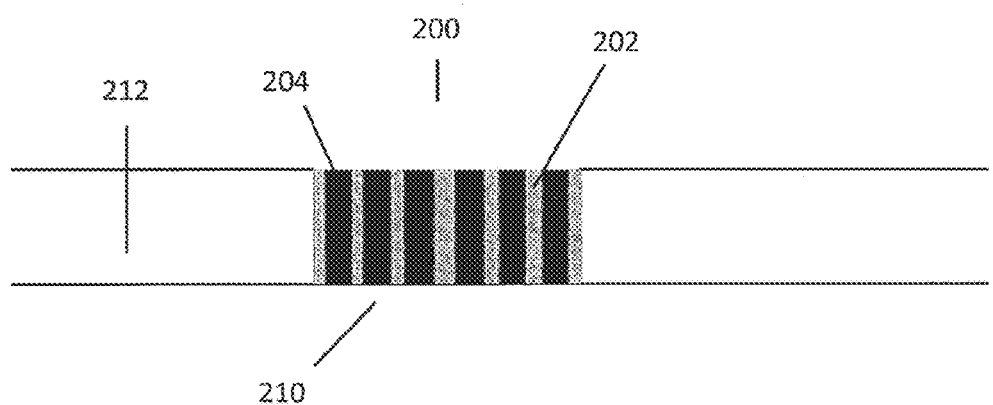
FIG. 2E is a cross-sectional view of a wound with another embodiment of a wound filler positioned therein.

FIG. 2E illustrates an embodiment of a wound filler similar to those described in FIG. 2A-2D, where the wound filler can be placed in an abdominal wound 210 surrounded by abdominal tissue 212. In some embodiments, the wound filler 200 comprises fill material 202 and extending members 204 similar to the embodiments described above. In certain embodiments, when negative pressure is applied, the wound filler 200 is configured to contract in the horizontal plane while remaining rigid in the vertical plane.

In any of the embodiments herein described, the wound filler can be cut to an appropriate shape and size to fit within the wound. The wound filler can be trimmed to shape in any manner, for example by trimming around the circumference of an oval wound filler or by trimming the horizontal edges of a square or rectangular wound filler.

In some embodiments, after the wound filler is appropriately sized, the extending members can be aligned such that, when placed in a wound cavity, they are perpendicular and extend in a vertical direction from the wound bed. In certain embodiments, application of a vacuum can then cause the fill material to contract substantially only in the horizontal plane, as the extending members reduce movement in the vertical direction (and may also resist horizontal movement). In some embodiments, the compression of the filler can aid in closing the wound cavity in the horizontal plane.

In some embodiments, preferably applicable to the embodiments described in FIGS. 2A-2E, the thickness of the extending members can range from 1 to 10 mm (or about 1 to about 10 mm), for example about 1 mm to about 2 mm, about 2 mm to about 3 mm, about 3 mm to about 4 mm, about 4 mm to about 5 mm, about 5 mm to about 6 mm, about 6 mm to about 7 mm, about 7 mm to about 8 mm, about 8 mm to about 9 mm, about 9 mm to about 10 mm, and greater than 10 mm (or greater than about 10 mm). In certain embodiments, the width of the fill material can range from 1 to 20 mm (or about 1 to about 20 mm), for example about 1 mm to about 5 mm, about 5 mm to about 10 mm, about 10 mm to about 1.5 mm, about 15 mm to about 20 mm, and greater than 20 mm (or greater than about 20 mm). In any of the embodiments described herein, the fill material may be adhered to the extending members. In certain embodiments, the fill material is adhered to the extending members by an adhesive. In certain preferable embodiments, the fill material is adhered to the extending members via Velcro™ tape.

In any of the embodiments described herein, the extending members can be made from rigid plastics such as polystyrene, polycarbonate, poly(meth)acrylates, semi-rigid materials such as silicone, or from rigid foams or felted flexible foams. In some embodiments, felted flexible foams can be made by subjecting flexible foams, e.g. those used as the porous compressible filler, to heat and pressure to produce a dense, semi-rigid foam that is still porous. Such a configuration can also enhance horizontal movement so as to permit greater wound closure.

In some embodiments (not shown but described as FIG. 2 in Provisional Application No. 61/651,483), a wound filler is provided comprising a minimally-compressible central core surrounded by a compressible outer layer. Such a configuration can reduce vertical movement and permit the wound edge to move inward in a direction toward the central core, thereby aiding in closing the wound. Further, the amount of closure can be controlled by varying the size of the central core. In some embodiments, the central core comprises one or more of a rigid foam, closed cell foam, and silicone elastomers or rigid flexible foam. Further embodiments may also comprise alternating concentric rings of more rigid (or more dense) material and less rigid (or less dense) material.

In certain embodiments (not shown but described as FIG. 3 in Provisional Application No. 61/651,483), an embodiment may be configured in the opposite manner as the embodiment described in the paragraph above, with a minimally-compressible outer layer surrounding a compressible core. The minimally-compressible outer layer can be configured to resist vertical compression, while the compression of the central core can aid in wound closure. As with the embodiment of the previous paragraph, this embodiment can be arranged in a concentric circle or oval configuration, or a linear configuration.

Figure 3A:
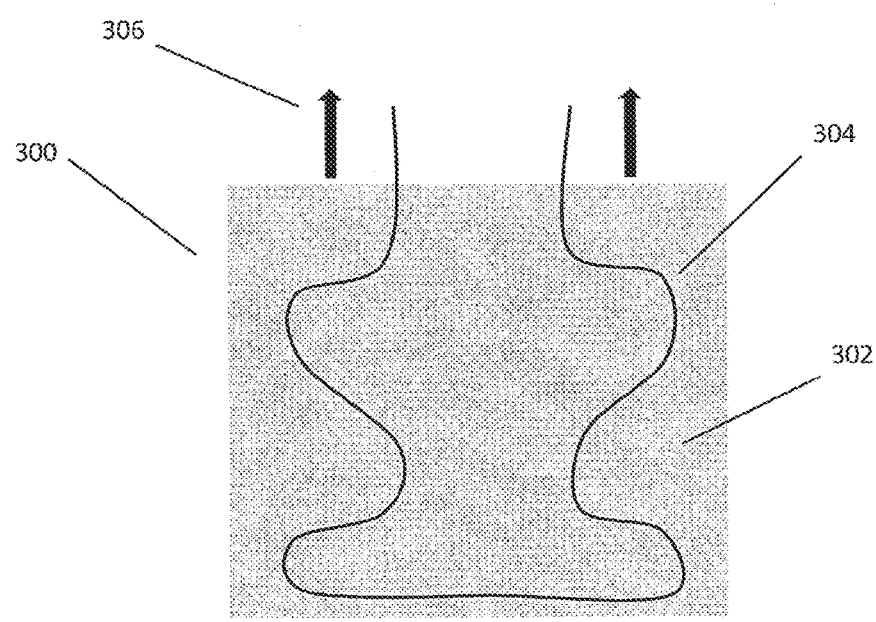
FIGS. 3A-C illustrate embodiments of wound fillers comprising one or more draw strings.

FIG. 3A illustrates an embodiment of a wound filler 300 comprising fill material 302 and one or more draw strings or cords 304. The one or more draw strings or cords can extend through the fill material, preferably with free ends extending from the top side of the wound filler (i.e., the side of the filler that will face outward when the wound filler is inserted into a wound). When negative pressure is applied using a system such as described above, the draw strings (which may extend out or under a wound cover) can be tightened, for example by pulling in a vertical direction 306, thereby causing the wound filler to contract substantially only in a horizontal plane.

Figure 3B:
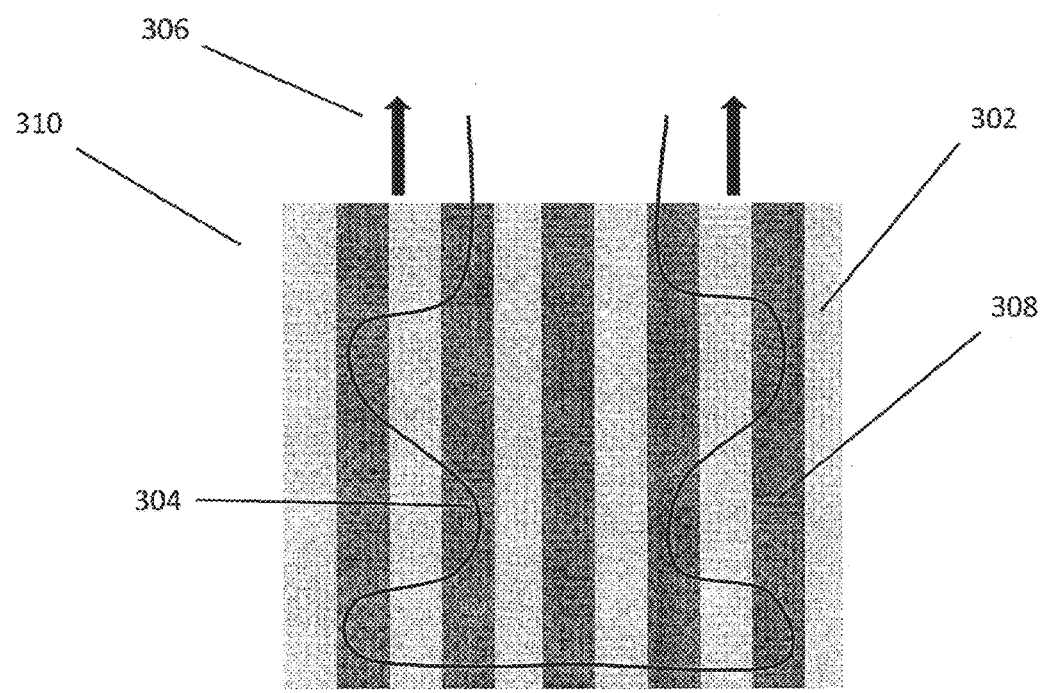

FIG. 3B illustrates an embodiment of a wound filler 310 comprising fill material 302 and extending members 308 such as described in any of the embodiments above, and one or more draw strings or cords 304. The one or more draw strings or cords extend through the wound filler 310, preferably with free ends extending from the top side of the wound filler. In a preferred embodiment, the fill material 302 and the extending members 308 can be alternating. In a similar manner to the embodiments described in FIGS. 2A-2E, the extending members 308 can be dense, more rigid, or more dense and rigid than the fill material. The one or more draw strings can extend through the wound filler, preferably with free ends extending from the top side of the wound filler (i.e., the side of the filler that will face outward when the wound filler is inserted into a wound).

In the embodiment of FIG. 3B, because the draw strings or cords 304 form loops between adjacent or spaced apart extending members 308, pulling of the draw strings can cause the extending members to compress the fill material therebetween and draw the extending members closer together. In some embodiments, the draw strings can be attached or secured at desired locations to the extending members 308 to facilitate the ability to draw the extending members closer together. In some embodiments, when negative pressure is applied using a system such as described above, the draw strings or cords can be tightened, for example by pulling in a vertical direction 306, thereby causing the wound filler to contract substantially only in a horizontal plane.

Figure 3C:
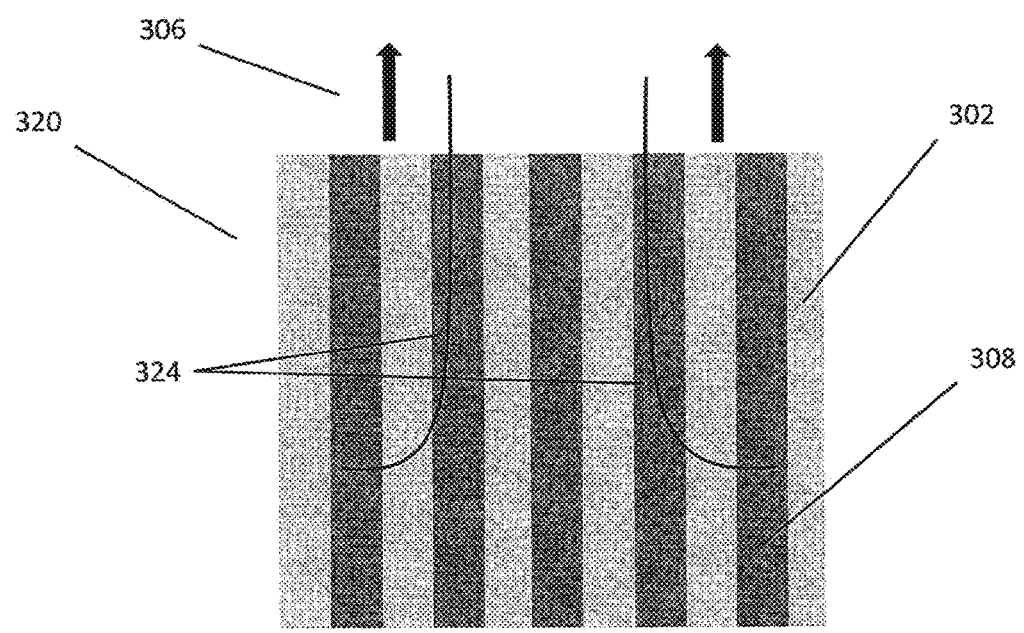
Figure 4A:
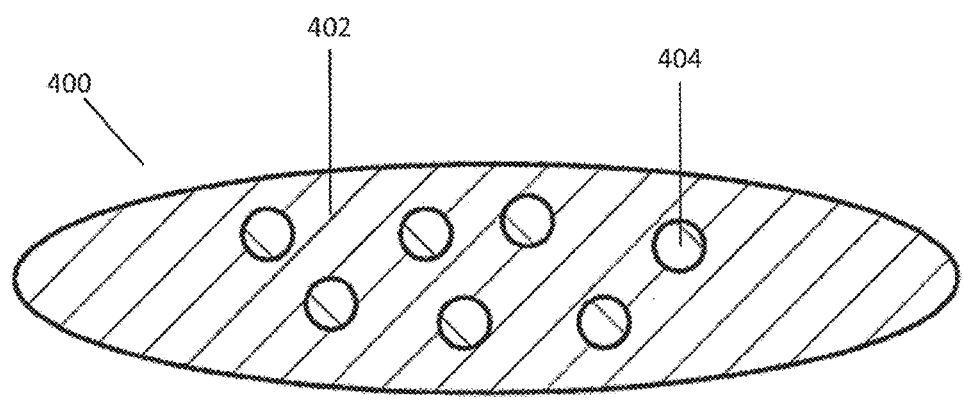
FIGS. 4A-B illustrate embodiments of a wound filler containing rigid columns or tiles.
Figure 4B:
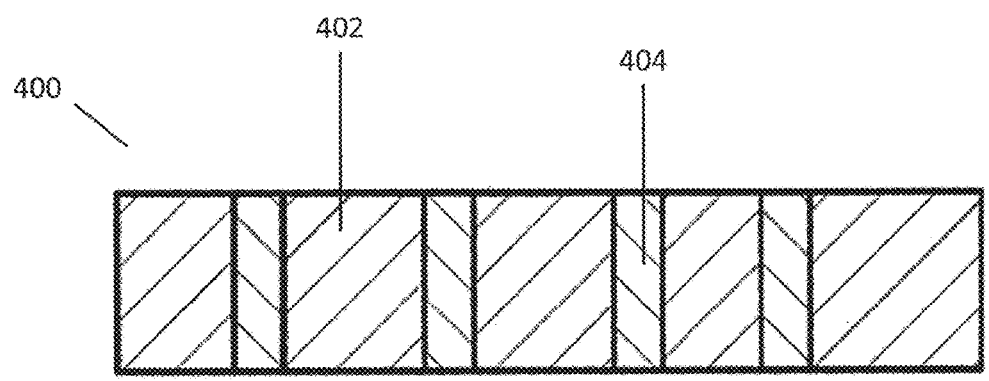

FIG. 3C illustrates an embodiment of a wound filler 320 similar to the embodiment described in FIG. 3B, comprising fill material 302, extending members 308, and multiple draw strings 324 configured to cause the wound filler 320 to contract in a horizontal direction. As illustrated, draw strings 324 may be secured to outer extending members 308, and may extend vertically through adjacent extending members out of the wound filler. In certain embodiments, when negative pressure is applied using a system such as described above, the draw strings or cords 324 can be tightened, for example by pulling in a vertical direction 306, thereby causing the wound filler to contract substantially only in a horizontal plane. In certain embodiments, the wound filler contains more than 2, more than 4, more than 6, or more than 8 draw strings or cords. FIGS. 4A-B illustrate different views of embodiments of a wound filler 400 similar to the embodiments described in FIGS. 2A-E. FIG. 4A depicts a horizontal cross-sectional view of a wound filler 400 comprising fill material 402 and extending members 404 extending in a vertical plane or direction. Preferably, the extending members can be rigid columns or tiles. In preferred embodiments, the wound filler will preferentially collapse horizontally when negative pressure is applied, while the rigid columns or tiles 404 substantially prevent the wound filler from collapsing vertically, thus assisting in wound closure. In some preferred embodiments, the wound filler 400 can be cut to the size of the wound, as the columns or tiles 404 are preferably dispersed throughout the wound filler. In a preferred embodiment, the fill material 402 comprises foam. FIG. 4B illustrates a vertical cross section of an embodiment of the wound filler described in FIG. 4A.

In some embodiments, the rigid columns can comprise rigid plastic such as polystyrene, polycarbonate or a semi-rigid material such as a silicone. In certain embodiments, the rigid columns can comprise a rigid or felted foam. In some embodiments, the columns may have a circular cross-section, and may have diameters for example from 5 mm to 10 mm (or about 5 mm to about 10 mm) with a spacing of 5 mm to 10 mm (or about 5 mm to about 10 mm) around them. For example, the diameter of the column can be about 1 mm, about 2 mm, about 3 mm, about 4 mm, about 5 mm, about 6 mm, about 7 mm, about 8 mm, about 9 mm, about 10 mm, or greater than 10 mm (or greater than about 10 mm). In certain embodiments, the spacing between the columns can range from about 1 mm to 5 mm, about 5 mm to 10 mm, about 10 mm to 15 mm, about 15 mm to 20 mm, or greater than 20 mm (or greater than about 20 mm).

In some embodiments (not shown but described as FIG. 14 in Provisional Application No. 61/651,483), a wound filler may comprise one or more conduits that extend to the wound-facing perimeter and are configured to communicate negative pressure. Here, once the wound is sealed under a drape, the one or more conduits can apply negative pressure to the wound, thereby contacting one or more areas on the inside perimeter of the wound. The wound filler can comprise fill material and extending members as described hereinbefore. The wound filler is preferably configured to contain one or more laces or filaments with free ends extending in a vertical direction away from the wound. Upon application of negative pressure, and once the edges of the wound have made contact with the wound filler, the one or more laces or filaments can be pulled so as to collapse the wound filler inward, thereby aiding in the closure of the wound. In some embodiments, the laces or filaments are attached to the extending members and may comprise any of the draw string embodiments previously described herein.

In some embodiments, any of the aforementioned wound fillers can comprise a dissolvable foam. In certain embodiments, the wound filler can comprise an area of dissolvable foam surrounding or surrounded by one or more regions of foam that do not dissolve under ordinary physiological conditions. In particular embodiments, the dissolvable foam region can be central and surrounded by one or more strips of non-dissolvable foam. In some embodiments, the dissolvable foam can also be in a ring configuration and surrounded at least on a horizontal plane by non-dissolvable foam (or vice-versa). In certain embodiments, when implanted into a wound, the dissolvable portions of foam can at least partly dissolve, for example upon contact with wound exudate, thereby providing additional space for the non-dissolvable foam to collapse toward. In preferable embodiments, this collapse can be used to promote horizontal closure of the wound. In some embodiments, the dissolvable foam can comprise polyvinyl alcohol foam (PVA).

In certain embodiments, the dissolvable foam can be replaced by a resorbable filler, for example a resorbable tissue filler scaffold. In some embodiments, this tissue filler can be constructed from biodegradable polymers such as polylactic acid, polyglycolic acid, or any combination of the two polymers. In particular embodiments, the resorbable scaffold can be configured to deliver beneficial molecules. In some embodiments, the scaffold is configured to deliver growth factors. In certain embodiments, the scaffold is configured to deliver antimicrobial molecules. In particular embodiments, such a scaffold can be seeded with beneficial cells, such as fibroblasts or stem cells. In some embodiments, such a scaffold can be seeded with keratinocytes.

In some embodiments, any of the aforementioned wound fillers can be constructed from a three-dimensional material comprising stiffer vertical components and compressible components extending in a lateral direction, such as 3D fabrics and fibers. In some embodiments, the material can present itself as a three-dimensional non-woven material. In particular embodiments, such a wound filler material can preferentially collapse or more readily collapse in a horizontal direction while resisting collapse in a vertical direction.

In some embodiments, any of the aforementioned wound filler materials can comprise a foam material with different-sized bubbles. In some embodiments, as smaller bubbles are more resistant to collapse than larger bubbles, the bubble sizes can be tailored to control the contraction of the wound filler. In certain embodiments, bubbles can be arranged in a gradient, such as a lengthwise or circular gradient, to control collapsibility of the wound filler. In certain embodiments, this arrangement of bubbles can be manufactured using a dual dispense injection process, wherein a first material having a first density (e.g., a first pore/bubble/void size) and a second material having a second density (e.g., a second pore/bubble/void size) are injected into a mold or a plurality of molds. In some embodiments, the second material can be the same material as the first material, but have a different pore size or different size voids or bubbles therein. In certain embodiments, foams of different pore, bubble, or void sizes or density can be coupled together.

Some embodiments can comprise foam with varying compressibility obtained by changing the chemistry or makeup of the material used to make the foam as foam is being produced. For example, without limitation, longer soft (more compressible) polymer blocks or plasticizers can be used to make all or a portion of the foam more compressible. In some embodiments, soft (more compressible) blocks or soft (more compressible) portions of the filler can be made from polypropylene glycol or polytetramethylene glycol, or other similar materials. In some embodiments, the filler can have soft (more compressible) blocks or soft (more compressible) portions made from any suitable sufficiently high molecular weight material.

In some embodiments, during manufacture of the foam material, the makeup of the material passing through the injectors or dispensers used to inject or dispense the foam material can be altered such that the density or stiffness of the foam changes along the length of the foam. For example, without limitation, the foam can be manufactured such that softer, more compressible portions are sandwiched or positioned between stiffer, less compressible portions of the same length of foam. Thereby, the foam having varying compressibility can be produced integrally. In certain embodiments, including any of the embodiments herein where the foam or filler can be produced in multiple stages, softer more compressible foam portions can be injected into, or otherwise inserted into voids or bubbles within a less compressible foam material, or vice versa, or can be formed (i.e., injected) or positioned between portions of less compressible foam material. In some embodiments, the additional material, if formed in separate foam blocks or layers, can be laminated or otherwise coupled with the other material or materials with which it is to be used.

In some embodiments, a method of treating a wound can include positioning any one of the aforementioned wound fillers into a wound bed and covering the wound filler with a wound cover. Applying negative pressure to such an embodiment can cause the wound filler to contract horizontally with the vertically extending members reducing vertical movement of the wound filler.

Other Negative Pressure Therapy Apparatuses Dressings Wound Fillers and Methods

Further embodiments of negative pressure therapy apparatuses, dressings, wound fillers and methods of using the same that may be utilized alone or in combination with the embodiments described herein, and further description of the embodiments found above, are found in U.S. Provisional Application No. 61/651,483, filed May 24, 2012, the entirety of which is hereby incorporated by reference. Portions of U.S. Provisional Application No. 61/651,483, which was included as an Appendix in U.S. Provisional Application No. 61/782,270, are reproduced below.

Figure 5A:
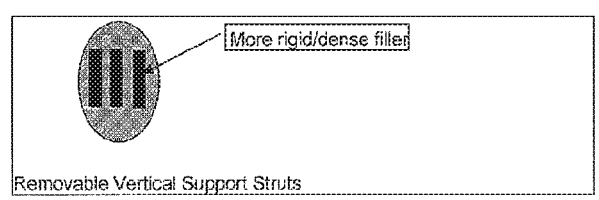
FIGS. 5A-22 illustrate further embodiments of the present application.
Figure 5B:
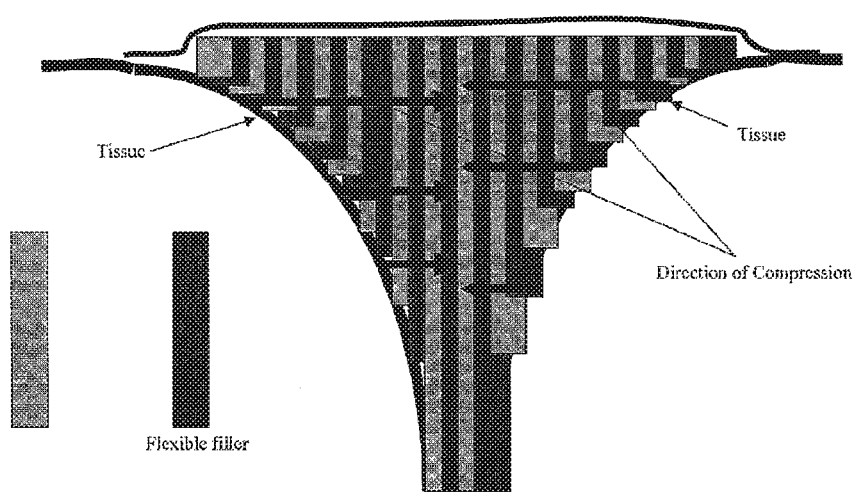
Figure 5C:
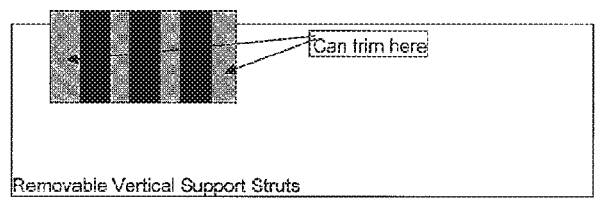

FIGS. 5A-5C illustrate embodiments of a porous wound filling material with slits or areas in which a denser porous wound filling material has been inserted, similar to the embodiments disclosed in FIGS. 2A-E. The embodiment is configured to be inserted into a wound. In some embodiments, the porous wound filling material is foam, for example an open-cell foam. The aforementioned embodiments can also enhance horizontal movement so as to permit greater wound closure.

Figure 6:
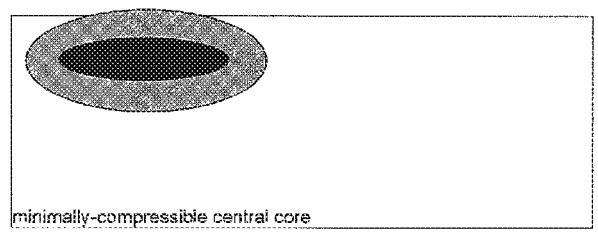

In a manner similar to the embodiment disclosed in FIG. 2B, FIG. 5B illustrates an embodiment of a wound filler material that can be cut to shape and can consist of alternate slabs of flexible or compressible wound filler (e.g., foam) together with more rigid wound filler. FIG. 6 illustrates a wound filler comprising a minimally-compressible central core surrounded by a compressible outer layer. Such a configuration can reduce vertical movement and permit the wound edge to move inward in a direction toward the central core, thereby aiding in closing the wound. Further, the amount of closure can be controlled by varying the size of the central core. In some embodiments, the central core comprises one or more of a rigid foam, closed cell foam, and silicone elastomers.

Figure 7:
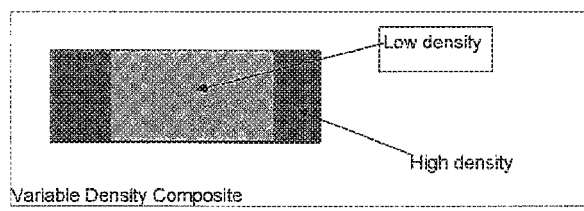
Figure 8:
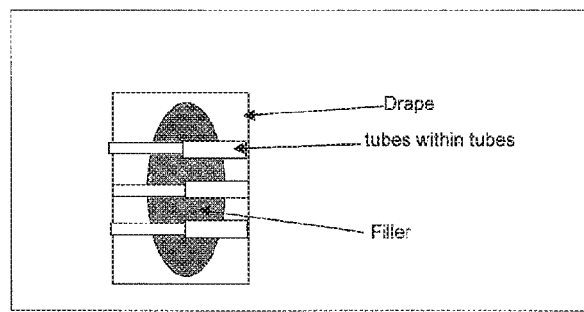

Figure 7 illustrates an embodiment that is configured in the opposite manner as FIG. 6 above, with a minimally-compressible outer layer surrounding a compressible core. The minimally-compressible outer layer can be configured to resist vertical compression, while the compression of the central core can aid in wound closure. As with FIG. 6, FIG. 7 can be arranged in a concentric circle or oval configuration, or a linear configuration.

In this embodiment, the treatment device comprises a wound filler (e.g., foam) with telescopic tubes. The wound filler can be placed into a wound cavity with telescopic tubes positioned across the major axis of the wound and on top of the filler and periwound area. In other embodiments, the tubes can be integrated through the wound filler. A drape can then be placed over the treatment device, and the entire assembly fluidically attached to a source of negative pressure.

Application of negative pressure will cause the filler to collapse in a horizontal plane, but the tubes will reduce vertical movement of the filler (which would otherwise apply a horizontal force that makes wound closure more difficult). As the wound margins contract, the telescopic tubes will collapse along their length, thus closing together with the wound.

Figure 9:
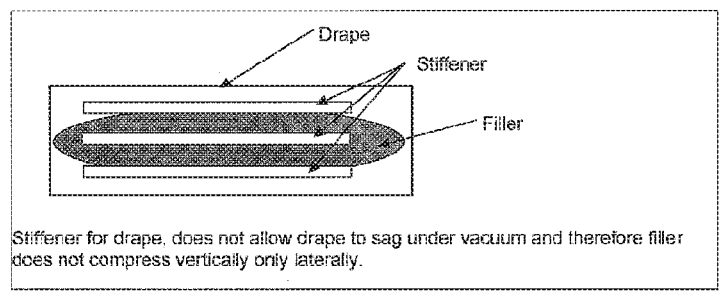

With reference to FIG. 9, in this embodiment, wound filling material such as foam is placed into a wound cavity. One or more stiffeners can then be placed over the wound, wound filler, and periwound area. The one or more stiffeners can be constructed from a rigid or semi-rigid material (such as a closed-cell foam) that resists compression. Application of a vacuum causes the foam to collapse in the horizontal plane, while the one or more stiffeners reduce vertical compression of the foam.

Figure 10:
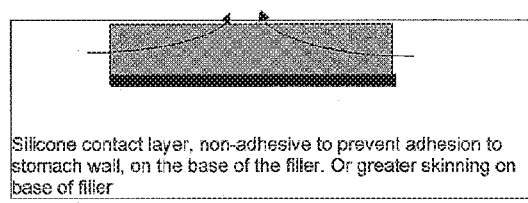

FIG. 10 illustrates an embodiment of a wound filler with a minimally-adherent wound contact layer on its base and configured to be placed in contact with the wound bed. In some embodiments, the wound contact layer can comprise silicone, or a foam with a thicker skin on one side. When vacuum is applied, the minimally-adherent wound contact layer would promote horizontal contraction of the foam so as to permit greater wound closure. Any of the embodiments disclosed herein, including without limitation those having foam or other fillers or wound packing, those having columns or struts or other support elements, can have a silicone or other slick material or film on one or more wound contacting surfaces thereof to reduce the adhesion or stickiness with respect to the wound.

Figure 11:
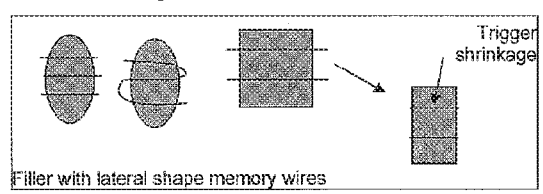

FIG. 11 illustrates an embodiment where a wound filler, which can be constructed from foam, comprises one or more threads or wires inserted therein. The wires preferably extend in a horizontal plane, and can be constructed from a shape-memory polymer or metal. The wires are preferably inserted or cast into the wound filler in an extended shape, and upon application of a stimulus, the wound filler preferentially contracts in the horizontal plane. In some embodiments, the stimulus causing contraction of the thread or wire can be moisture, heat, or application of reduced pressure.

In some embodiments, the wound filler can comprise entirely or in part an elastomeric shape-memory foam. The shape-memory foam can be pre-stressed into an extended configuration, and, upon exposure to moisture, will contract. An example of a suitable shape-memory foam is Elast-Eon™.

In this embodiment, a wound filler has one or more draw strings or cords extending through it, preferably with free ends extending from the top side of the wound filler (i.e., the side of the filler that will face outward when the wound filler is inserted into a wound). When negative pressure is applied, the draw strings can be tightened, for example by pulling in a vertical direction, thereby causing the foam to contract substantially only in a horizontal plane.

Figure 12:
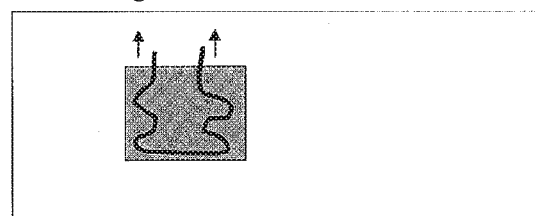

FIG. 12 illustrates an embodiment similar to the embodiment described in FIG. 3A-C. Draw strings or cords may extend through the structure. The drawstrings tighten under negative pressure and cause the structure to contract in only one plane.

Figure 13:
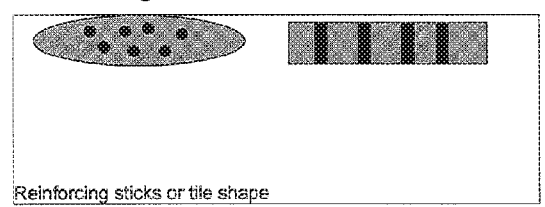

FIG. 13 illustrates an embodiment with a wound filler material with rigid columns or tiles extending in a vertical plane or direction, an embodiment similar to the embodiments described in FIGS. 4A-B. The wound filler, which can comprise foam, will preferentially collapse horizontally when negative pressure is applied. The rigid columns or tiles will substantially prevent the wound filler from collapsing vertically, thus assisting in wound closure. Advantageously, the wound filler can be cut to the size of the wound, as the columns or tiles are preferably dispersed throughout the wound filler.

Figure 14:
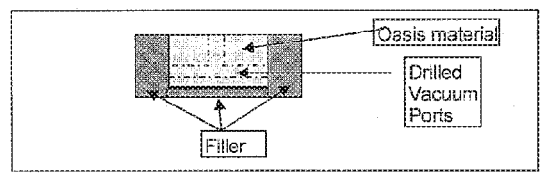

FIG. 14 illustrates an embodiment of a wound closure device comprising a rigid oasis, or core, surrounded by a soft, conformable wound filler such as a reticulated foam. The core comprises one or more passages communicating between the filler material and a source of negative pressure. Upon application of negative pressure, the wound filler will collapse toward the core, thereby preferentially collapsing in a horizontal plane and facilitating wound closure. In one embodiment, the core comprises a central conduit configured to be connected to the source of negative pressure (e.g., via a conduit or a miniature pump), where the central conduit links to one or more peripheral conduits in fluidic communication with the filler.

Figure 15:
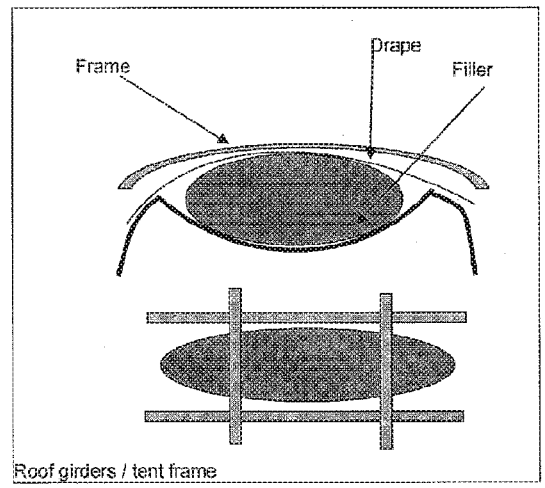

FIG. 15 illustrates an embodiment of a wound closure system comprising a wound filler placed inside a wound and overlaid with a drape and frame. The frame can be placed or assembled over the foam and onto the periwound area outside of the drape, and attaches to the drape so as to restrict vertical movement of the drape and wound filler. Accordingly, horizontal collapse of the filler will be maximized.

Figure 16A:
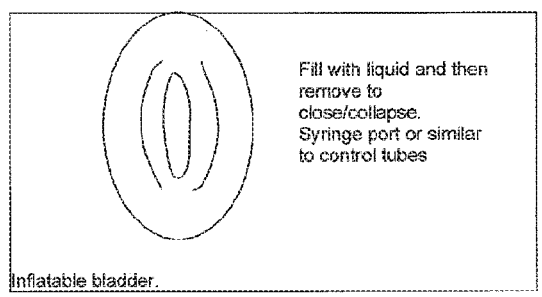

With reference to FIG. 16A, this embodiment can have an inflatable bladder surrounded at least in part by a porous wound filler material such as foam. The inflatable bladder can be filled with liquid, and preferably comprises one or more ports (e.g., a syringe port) that can be used to adjust the amount of fluid therein. In use, the device is placed into a wound and covered with a drape, and, upon application of negative pressure, fluid can be withdrawn from the inflatable bladder to control the amount of contraction of the wound margins. Preferably, the fluid is withdrawn via a tube connected through or under the drape that connects the port to a different source of negative pressure such as a syringe.

Figure 16B:
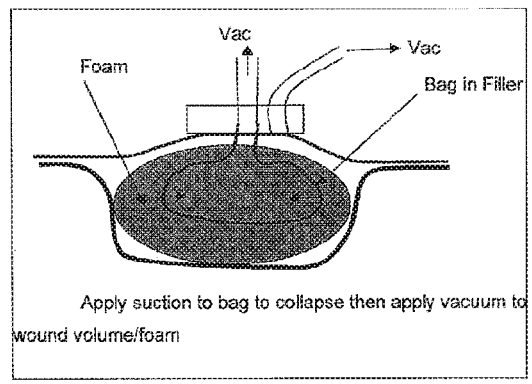

In a manner similar to the embodiment illustrated in FIG. 16A, FIG. 16B illustrates an embodiment with an inflatable bag surrounded at least in part by a wound filler such as foam. Here, the inflatable bag is filled with air or gas, and suction (separate from a source of negative pressure used to treat the wound) can be applied to control the amount of contraction of the foam.

Figure 17:
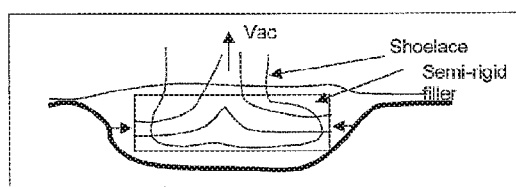

FIG. 17 illustrates a semi-rigid wound filler comprising one or more conduits extending to a wound-facing perimeter of the filler that are configured to communicate negative pressure. Here, once the wound is sealed under a drape, the one or more conduits apply negative pressure to the wound, thereby contacting one or more areas on the inside perimeter of the wound. The semi-rigid wound filler is preferably configured to contain one or more laces or filaments with free ends extending in a vertical direction away from the wound. Upon application of negative pressure, and once the edges of the wound have made contact with the wound filler, the laces can be pulled so as to collapse the wound filler, thereby aiding in the closure of the wound.

Figure 18:

In FIG. 18, an embodiment of a wound filler such as foam can have its outside (wound-facing) edges cut to provide additional surface area and protrusions to aid in fixation to the wound surface. These edges can consequently enhance wound closure by aiding in pulling the wound edges together upon the application of negative pressure. For example, pinking shears or other serrated cutting implements can be used to add a sawtoothed, wavy, corrugated, irregular, or roughened outer perimeter to the wound filler. Other embodiments can provide for grit-blasting, sanding, or adding particulates to the surface of the wound filler.

Figure 19:
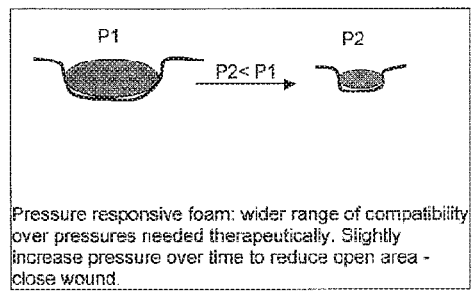

FIG. 19 illustrates an embodiment of a pressure responsive foam for use in a wound. Upon application of negative pressure, conventional foams tend to collapse to approximately the same dimensions over the therapeutic ranges of negative pressure applied thereto. However, by tailoring a pressure responsive foam where the volume changes across the therapeutic range of negative pressure, greater control over wound closure can be achieved. For example, such a foam can have a given volume $V_1$ at a given pressure $P_1$. If the negative pressure is increased to a new pressure $P_2$, the foam's volume can decrease to a new volume $V_2$ that is smaller than $V_1$. Accordingly, wound closure can be controlled by application of negative pressure to the wound.

Figure 20:
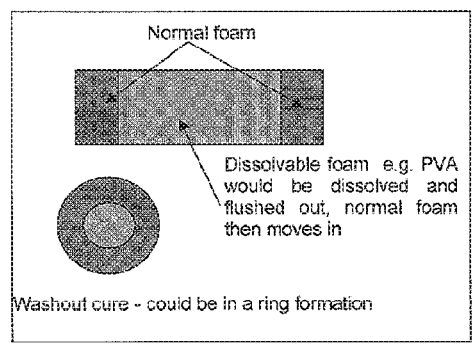

FIG. 20 illustrates an embodiment of a wound filler comprising a dissolvable foam. Here, the wound filler can comprise an area of dissolvable foam surrounding or surrounded by one or more regions of foam that do not dissolve under ordinary physiological conditions. In some configurations, the dissolvable foam region can be central and surrounded by one or more strips of non-dissolvable foam. The dissolvable foam can also be in a ring configuration and surrounded at least on a horizontal plane by non-dissolvable foam (or vice-versa). When implanted into a wound, the dissolvable portions of foam would at least partly dissolve, for example upon contact with wound exudate, thereby providing additional space for the non-dissolvable foam to collapse toward. This can be used to promote horizontal closure of the wound. In some embodiments, the dissolvable foam can comprise polyvinyl alcohol foam (PVA). In some embodiments, the dissolvable foam can be replaced by a resorbable filler, for example a resorbable tissue filler scaffold. In some embodiments, such a scaffold can be seeded with beneficial cells, such as fibroblasts or stem cells.

Figure 21:
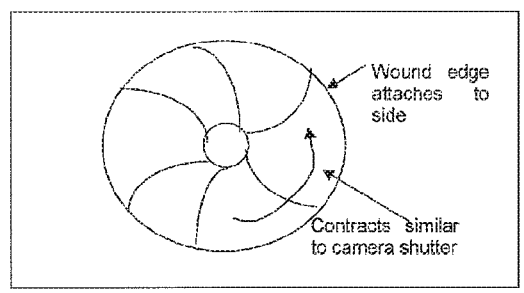

FIG. 21 illustrates an embodiment of a wound closure device comprising a camera-shutter or iris-like configuration of multiple pieces of wound filler material. Preferably, the wound filler material is substantially rigid at least in a vertical plane. The multiple pieces of wound filler material are preferably configured to move inward from an open configuration illustrated above to a closed configuration upon the application of negative pressure, thereby contracting the wound margins in a horizontal plane. The inward movement of the multiple pieces of wound filler material may resemble the inward movement of a camera shutter.

Figure 22:
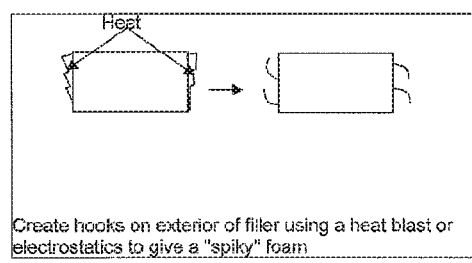

FIG. 22 illustrates an embodiment of a wound filler device comprising one or more hooks disposed on an outer perimeter thereof, and preferably along a horizontal outer perimeter. The one or more hooks are configured to engage the edges of a wound so as to aid attachment of the filler, thereby aiding in wound closure upon the application of negative pressure. The one or more hooks can be made by using a sudden localized "blast" of heat that can partly melt the foam edge so as to produce a spike, hook, or other protrusion. Application of electrostatic energy to the wound filler can also be used to make the one or more hooks.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A wound filler for use in treating a wound with negative pressure, comprising:
    a porous wound filling material; and
    a plurality of sheets or slabs configured to extend vertically and lengthwise across a wound bed when the wound filler is positioned within the wound bed, the plurality of sheets or slabs being made of a more rigid material than the porous wound filling material;
    wherein the plurality of sheets or slabs are spaced apart and dispersed throughout the wound filler in a horizontal plane;
    wherein the plurality of sheets or slabs are fully surrounded by the porous wound filling material in the horizontal plane and the porous wound filling material extends between the plurality of sheets or slabs;
    wherein the sheets or slabs are aligned parallel to one another; and
    wherein upon application of negative pressure to the wound filler, the wound filler is configured to contract horizontally with the sheets or slabs reducing vertical movement of the wound filler.

2. The wound filler of claim 1, wherein the porous wound filling material surrounds the plurality of sheets or slabs.

3. The wound filler of claim 1, wherein the porous wound filling material comprises a plurality of slits or areas in which the plurality of sheets or slabs are inserted.

4. The wound filler of claim 1, wherein flexible material is positioned between the sheets or slabs to allow compression of the sheets or slabs towards each other in a horizontal plane when the wound filler is positioned within a wound bed and is placed under negative pressure.

5. The wound filler of claim 1, wherein the plurality of sheets or slabs are adhered to the porous wound filling material.

6. The wound filler of claim 1, further comprising one or more draw strings or cords extending through the wound filler configured such that pulling of the draw strings will cause contracting of the wound filler in a horizontal plane.

7. The wound filler of claim 1, wherein the sheets or slabs are spaced apart equally in the wound filler when the wound filler is positioned within a wound bed.

8. The wound filler of claim 1, wherein the sheets or slabs are spaced apart unequally in the wound filler when the wound filler is positioned within a wound bed.

9. The wound filler of claim 1, wherein the sheets or slabs and the wound filling material are portions of material that are substantially parallel to one another and alternatingly stacked adjacent to one another.

10. A negative pressure wound therapy system, comprising:
    the wound filler of claim 1; and
    a wound cover configured to be placed over the wound filler.

11. The system of claim 10, further comprising a connection for connecting the wound cover to a source of negative pressure.

12. The system of claim 10, further comprising a negative pressure source configured to be connected to the wound cover to provide negative pressure to the wound filler when placed within the wound bed.

13. A method of treating a wound, comprising:
    positioning the wound filler of claim 1 into a wound bed;
    covering the wound filler with a wound cover; and
    applying negative pressure to the wound cover, wherein the application of negative pressure causes the wound filler to contract horizontally with the sheets or slabs reducing vertical movement of the wound filler.

* * * * *